United States Patent
Pierangelo et al.

(10) Patent No.: US 12,396,619 B2
(45) Date of Patent: Aug. 26, 2025

(54) SYSTEM FOR POLARIMETRIC CHARACTERIZATION OF A TARGET

(71) Applicants: Ecole Polytechnique, Palaiseau (FR); CENTRE NATIONAL DE LA RECHERCHE SCIENTIFIQUE, Paris (FR)

(72) Inventors: Angelo Pierangelo, Palaiseau (FR); Arvid Olof Lindberg, Palaiseau (FR)

(73) Assignees: ECOLE POLYTECHNIQUE, Palaiseau (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 117 days.

(21) Appl. No.: 17/796,749

(22) PCT Filed: Feb. 4, 2021

(86) PCT No.: PCT/EP2021/052647
§ 371 (c)(1),
(2) Date: Aug. 1, 2022

(87) PCT Pub. No.: WO2021/156356
PCT Pub. Date: Aug. 12, 2021

(65) Prior Publication Data
US 2023/0083663 A1 Mar. 16, 2023

(30) Foreign Application Priority Data
Feb. 4, 2020 (EP) .................................... 20305099

(51) Int. Cl.
*G01N 21/65* (2006.01)
*A61B 1/00* (2006.01)
(Continued)

(52) U.S. Cl.
CPC ........ *A61B 1/00009* (2013.01); *A61B 5/0084* (2013.01); *A61B 1/00078* (2013.01);
(Continued)

(58) Field of Classification Search
CPC .............. A61B 1/00009; A61B 5/0084; A61B 1/00078; A61B 1/002; A61B 1/0646;
(Continued)

(56) References Cited

U.S. PATENT DOCUMENTS 5,608,834 A    3/1997  Van Leeuwen
6,537,211 B1*  3/2003  Wang .................. A61B 1/0005
                                                            600/178
(Continued)

FOREIGN PATENT DOCUMENTS

CN    104161493 B        4/2016
CN    110514598 A    *  11/2019
(Continued)

OTHER PUBLICATIONS

International Search Report (ISR) for PCT/EP2021/052647 mailed Feb. 23, 2021 (4 pages).
(Continued)

*Primary Examiner* — Michelle M Iacoletti
*Assistant Examiner* — Maher Yazback
(74) *Attorney, Agent, or Firm* — Jason A. Smith, Esq.; Shumaker, Loop & Kendrick, LLP

(57) ABSTRACT

A system for polarimetric characterization of a target that includes a liquid light guide (LLG) for propagating light from a light source to the target (S) at least one of a Polarization State Analyzer (PSA) serving to analyze polarization of light having propagated into the LLG and that has been reflected by the target, and a Polarized State Generator (PSG) for modulating the polarization of light injected into
(Continued)

the LLG, an optical detector for detecting light backscattered by the target (S) that has been illuminated by the LLG.

21 Claims, 3 Drawing Sheets

(51) Int. Cl.
*A61B 5/00* (2006.01)
*A61B 1/002* (2006.01)
*A61B 1/06* (2006.01)
*A61B 1/07* (2006.01)

(52) U.S. Cl.
CPC .............. *A61B 1/002* (2013.01); *A61B 1/0646* (2013.01); *A61B 1/07* (2013.01); *A61B 2562/0238* (2013.01); *A61B 2576/00* (2013.01)

(58) Field of Classification Search
CPC .............. A61B 1/07; A61B 2562/0238; A61B 2576/00; A61B 1/00117; A61B 1/00165; A61B 1/00186; A61B 1/043; A61B 1/055; G02B 6/024; G02B 2006/0325; G02B 6/032; G02B 23/2469; G02B 23/2484; G01N 21/21
See application file for complete search history.

(56) References Cited

U.S. PATENT DOCUMENTS

| | | | |
|---|---|---|---|
| 10,094,766 B2* | 10/2018 | De Martino | G01N 21/21 |
| 2006/0184037 A1 | 8/2006 | Ince et al. | |
| 2017/0224205 A1* | 8/2017 | Sunar | A61B 1/0684 |
| 2018/0252695 A1* | 9/2018 | Huang | G01N 21/4738 |
| 2022/0142458 A1* | 5/2022 | Kashima | A61B 1/000096 |
| 2022/0171332 A1* | 6/2022 | Cuche | G03H 1/0005 |

FOREIGN PATENT DOCUMENTS

| | | | | |
|---|---|---|---|---|
| EP | 2228003 A1 * | 9/2010 | ......... | A61B 1/00009 |
| JP | 2008522185 A | 6/2008 | | |
| JP | 2012-24252 A | 2/2012 | | |
| JP | 2017512989 A | 5/2017 | | |
| WO | 2018/126497 A1 | 7/2018 | | |
| WO | WO-2018207569 A1 * | 11/2018 | ......... | A61B 1/00064 |

OTHER PUBLICATIONS

Written Opinion for PCTPCT/EP2021/052647 mailed Feb. 23, 2021 (6 pages).

J. Qi et al "Narrow band 3x3 Mueller polarimetric endoscopy" Biomed. Opt. Express 4, 2433-49 (2013).

J. Qi et al in "A high definition Mueller polarimetric endoscope for tissue characterization" Sci. Rep. 6, 25953 (2016).

Vizet et al., "Demonstration of Mueller polarimetry through an optical fiber for endoscopic applications" 2014 Conference on Lasers and Electro-Optics (CLEO)—Laser Science to Photonic Applications, The Optical Society, dated Jun. 8, 2014 ( 2 pages).

Fu et al., "Flexible 3 x 3 Mueller Matrix Endoscope Prototype for Cancer Detection", Mar. 2018, IEEE Transactions on Instrumentation and Measurement PP(99)1-13.

Lindberg et al., "Mueller polarimetric imaging through a rigid endoscope", Proc. SPIE-OSA vol. 11073, Clinical and Preclinical Optical Diagnostics II, 110730F (Jul. 19, 2019); doi: 10.1117/12.2526384 (4 pages).

Office Action (OA) for Japanese Patent App. No. 2022-547104; issued on Jan. 8, 2025; 7 pages.

* cited by examiner

SYSTEM FOR POLARIMETRIC CHARACTERIZATION OF A TARGET

The present invention relates to a system for polarimetric characterization of a target and to a related method. More particularly, but not exclusively, it relates to in vivo endoscopic Mueller polarimetric characterization of biological tissues.

BACKGROUND

Endoscopes are imaging tools widely used in many diagnostic and surgical biomedical applications. Narrow and difficult zones to reach in human body cavities (colon, stomach, lung, etc.) can be visualized with high resolution and minimal invasiveness by the means of such systems. They are commonly used by practitioners to identify suspect areas where biopsies are performed in order to confirm the presence of cancerous or precancerous lesions, as well as during surgery for their resection. The accurate determination of the zones to biopsy is crucial for getting the correct diagnosis, identifying the most appropriate treatment and for enabling a quick management of a patient. In the same way, the clear identification of the surgical margins of pathological parts is crucial to completely remove them, sparing as much healthy tissues as possible.

Flexible endoscopes typically rely on fiber optics or chip-on-a tip-designs and are used to reach internal parts of the human body passing through tubular structures characterized by strong curvatures such as stomach or esophagus, small intestine, colon, etc.

Rigid type endoscopes, on the other hand, such as laparoscopes, are non-flexible straight tubes which are whenever possible preferable to flexible endoscopes because of their superior image quality and sterilization properties. They are more convenient for examining non tubular structures, such as the abdominal cavity, the thoracic cavity, etc.

Most endoscopes currently in use in medical practice are based on white visible light which is not very specific for detecting cancerous or precancerous areas. For this reason, pathological parts to biopsy or to remove during surgery can be easily missed by practitioners, with very important consequences for patients. Failure to properly determine the surgical margins, for example, increases the possibility of cancer recurrence and can require supplementary surgery and treatment.

Contrast enhancing techniques are therefore necessary to improve endoscopic systems.

Mueller polarimetric imaging improves contrast for cancer detection on different types of tissues.

A conventional Mueller matrix of a sample operates on a 4×1 Stokes vector which represents an incident polarization state falling on the sample to create a transformed 4×1 Stokes vector which represents a backscattered polarization state coming from the sample. The Mueller matrix is usually a 4×4 matrix with real coefficients which represents the signature of the complete polarimetric response of a sample. In some instances, the considered Mueller matrix can be a 3×3 incomplete matrix containing less information.

Mueller polarimetric characterization of a sample thus provides polarimetric information that has been shown to enhance the contrast for a variety of biological tissues and proves helpful to identify pathological parts, such as precancerous and cancerous lesions.

Mueller polarimetry relies on the use of a Polarization State Generator (PSG) and a Polarization State Analyzer (PSA).

In vivo use of Mueller polarimetry requires that the system is capable of sequentially acquiring at least 16 intensity images, needed to extract the complete Mueller matrix of the target, in less than about 2 s, in order to reduce the movement artifacts and provide wide-field images, preferably up to several $cm^2$ for applications to biomedical diagnostics.

In conventional endoscopes, light is delivered to the distal end of the endoscope by a bundle of optical fibers wrapped around an imaging channel, both being enclosed in a stainless-steel tubular body that can withstand autoclaving sterilization. Illumination of the target through the PSG placed at the proximal fiber port of the endoscope is not possible because of the depolarization effect of the fiber bundle. In most known systems, the PSG and the PSA are both fitted at the distal tip of the endoscope, which raises serious compactness and sterilization issues.

Some proposals have been made by Y. Fu et al in the article "Flexible 3×3 Mueller matrix endoscope prototype for cancer detection", IEEE Trans. rostrum. Meas. 67, (2018) or by Qi et al "Narrow band 3×3 Mueller polarimetric endoscopy" Biomed. Opt. Express 4, 2433-49 (2013), relying on the determination of a 3×3 Mueller matrix.

Another proposed solution is disclosed by J. Qi et al in "A high definition Mueller polarimetric endoscope for tissue characterization" Sci. Rep. 6, 25953 (2016) that consists in integrating the PSG components into a sheath surrounding the endoscope which a motor rotates. This solution is not practical for clinical settings as the image acquisition is too slow, due to the need of rotating the sheath. Moreover, the mechanical movements make the system unstable and then difficult to use in medical practice.

International application WO2018/126497 discloses an endoscopic system in which the distal tip of the endoscope is equipped with a PSG and a PSA having rotating components.

Patent application JP 2012-24252 discloses various endoscopic systems for Mueller polarimetry. In some systems, the imaging and illumination channels are separated and angled one with respect to the other, which necessitates two different introduction paths into the body. In some other systems disclosed in this application, the polarized light is introduced at the proximal end of a single optical fiber, which limits the intensity of light illuminating the target. Some other systems use a single optical fiber for signal collection. Such systems enable to perform a punctual polarimetric measurement. Indeed, the use of a single optical fiber does not allow to make an image unless a scan is carried out, which considerably increases the acquisition time to produce a macroscopic image. In order to produce an image in less than 2 s (time compatible with applications in vivo) the size of the obtained image is very small (~100 µm), which makes it completely unusable for applications in vivo.

Single-mode silica optical fibers transport very small amount of light. Multimode silica optical fibers enable to transport more light but are strongly depolarizing. Bundles of multimode silica optical fibers may enable to bring more light to the target. However, the spaces between the individual fibers remain unused. These dead spots do not transmit the light thus considerably decreasing the transmission efficiency of the bundle. Moreover the bundle may be damaged quite easily. Finally it completely depolarizes transported light.

The proceedings entitled "Mueller polarimetric imaging through a rigid endoscope" by Arvid Linderg et al, published at the European Conference on Biomedical Optics, Munich, Germany Aug. 27, 2019, discloses an experimental setup for Mueller polarimetric characterization of the imaging channel of a conventional rigid endoscope. The PSG is placed downstream of a light guide to illuminate a sandblasted metallic plate that is imaged by the endoscope.

U.S. Pat. No. 5,608,834 discloses a liquid light guide for endoscopic use. However, this patent is silent about any polarimetric properties of the liquid light guide.

SUMMARY OF THE INVENTION

The invention aims to improve polarimetric systems and to remedy to at least sonic of the deficiencies of the prior art identified above.

Exemplary embodiments of the invention relate to a system for polarimetric characterization of a target, comprising:
- a liquid light guide (LLG) for propagating light from a light source to the target (S),
- at least one of:
  - a Polarization State Analyzer (PSA) serving to analyze the polarization of the light having propagated into the LLG and that has been reflected by the target, and
  - a Polarization State Generator (PSG) for modulating the polarization of the light injected into the LLG,
- an optical detector for detection the light backscattered by the target that has been illuminated by the LLG.

Such detection can be carried out for at least two different probe states of the PSA and/or PSG.

The invention enables Mueller polarimetry to be carried out, as well as other polarimetry techniques such as Stokes polarimetry and Orthogonal. State Contrast (OSC), depending on the application and on the polarimetric parameters that are to be generated. The invention enables to measure a 4×4 or 3×3 Mueller matrix. It may use all or a fraction (at least one) of the coefficients of measured Mueller matrix as parameters of interest. It may also use a combination of these parameters. Other polarimetric parameters can be obtained from measured Mueller matrix, such as the depolarization index, the purity indices, the entropy, etc. The Mueller matrix can be decomposed to extract some polarimetric parameters such as depolarization, retardance or dichroism. Different types of decompositions of Mueller matrices can be used such as the Lu-Chipman decomposition, the Symmetric decomposition or the Reverse decomposition, inter alia.

The number of different polarization probe states of the PSA and/or PSG will be selected depending on the type of polarimetric detection selected and also on the polarimetric parameters of interest.

By Mueller polarimetric characterization it is meant the determination of at least 3×3 coefficients of the Mueller matrix, and more preferably the 4×4 coefficients of a complete Mueller matrix.

By Stokes polarimetry it is meant the determination of Stokes parameters.

The LLG allows delivering light with high intensity and spatial uniformity with respect to conventional silica optical fiber bundle, which proves advantageous for in vivo polarimetry. Furthermore, the quantity of light can be increased, thus enabling a larger surface of the target to be analyzed.

Unlike a bundle of optical fibers, the LLG does not depolarize the light in a significant way. The use of the LLG enables to: i) modulate the polarization of the light near the proximal end of the LLG; ii) effectively transport the polarized light until the surface under examination, without the need for insertion of integrated optics on the path of light near the distal end of the LLG which is close to the surface under examination. When applied to the endoscopy, this enables to obtain a compact endoscope.

The invention also enables, if desired, to have access to all the polarimetric information of a biological sample by virtue of the complete determination of the 4×4 Mueller matrix of the target under observation and to perform rapid and multispectral Mueller polarimetric imaging of biological tissues with a relatively low error, for example lower than 1%.

Furthermore, the invention does not require an additional incision for the illumination and minimally modifies endoscopic surgery and can use standard endoscopic white light sources. By changing a bandpass filter, for example placed upstream of the optical detector, the operating wavelength can be easily modified. Using a tri-CCD or tri-CMOS camera, coupled with a tri-band filter, one can acquire polarimetric images at three different wavelengths, for example in the blue, green and red parts of the visible spectral range. Using particular tri-CCD or tri-CMOS cameras, it is possible to extend the spectral range of interest also to the near infrared until approximately 1000 nm.

In some embodiments, the system comprises a detection channel in which light propagates before reaching the optical detector, in particular a detection channel comprising an optical relay such as a succession of rod lenses, as it is the case in a conventional rigid endoscope, or a detection channel made by an LLG that is different from the LLG serving to illuminate the target. The LLG may extend in a rigid tubular body, made of stainless steel for example.

The detection channel may be an imaging channel, allowing to take images of the target with the optical detector, which is in this case a camera.

In some embodiments, the LLG extends along the detection channel. The LLG may extend at least on part of its length parallel to the detection channel.

The detection channel may extend in a rigid casing, the casing preferably comprising a tubular body, preferably made of stainless steel, in which preferably both the detection channel and the liquid light guide extend.

For Mueller polarimetry, inter alia, the system comprises a PSG through which light is injected into the LLG and a PSA through which light is reaching the optical detector.

In some embodiments, light backscattered by the target is collected directly by the optical detector without propagating through a LLG or a detection channel comprising an optical relay such as a succession of rod lenses, for example an imaging channel of an endoscope.

The system may comprise a bandpass filter for narrowing the bandwidth of the light that is reaching the optical detector. The bandwidth preferably is no greater than 30 nm FWHM, better no greater than 20 nm FWHM. The system may be configured for acquiring light at two or more different wavelengths and for computing Mueller parameters or other polarimetric parameters at these wavelengths.

The PSG and/or PSA preferably comprise ferroelectric liquid crystals. These allow reducing the acquisition time and obtain a wide field of view. Other modulators may also be used such as nematic liquid crystals and photo-elastic modulators, inter alia, as detailed below.

The polarimetric system may comprise a control system to control the PSG and/or PSA, record signals, in particular images, from the optical detector, compute Stokes parameters, the Mueller matrix or the USC image of the target and display corresponding information.

The optical detector may be a monochromatic CCD or CMOS camera or a multichromatic camera such as a tri- CCD or tri-CMOS camera or a hyperspectral camera. The optical detector may also be a single photodiode or a spectrometer.

Polarimetric images, where the brightness or color of each pixel represents a value of the measured Mueller matrix or a corresponding polarimetric parameter, such as depolarization, retardance or dichroism, or all possible other polarimetric parameters, or combination thereof, may be displayed. The images may be displayed in rows and/or columns. Histograms of intensity, depolarization, retardance and dichroism, inter alia, or combination thereof, calculated for the whole or part of the target, may also be displayed. Various parameters can be extracted from the measured Mueller matrix such as the depolarization index, the indices of purity, the entropy, etc. Other parameters such as depolarization retardance and dichroism can be extracted from measured Mueller matrix by using different types of decompositions.

The wording "control system" is to be understood with a broad meaning and encompasses any data processing equipment configured for performing the required operations and actions, such as a personal computer, a microcomputer, a Field Programmable Gate Array (FPGA), a microcontroller or dedicated electronic circuit, with any desired control circuits or human machine interface, such as a display, a keyboard, control buttons, etc. This equipment may be local or distant and part of the control or data processing may be performed through a communication channel such as Internet or mobile networks.

The control system may operate a program to compute the Mueller matrix or any other polarimetric information of the target based on the detected intensities for different polarization states of the PSG and/or PSA and information obtained during prior calibration of the polarimetric system.

The control system may operate a program to compute various polarization parameters based on the Mueller matrix of the target by using different types of data treatment (Decomposition of Mueller matrices, Machine Learning algorithms, Adaptive Polarimetry, etc.). The polarimetric information may be computed for each pixel of a digital image and an array of images may be displayed simultaneously, each image carrying corresponding polarimetric information.

Exemplary embodiments of the invention also relate to a method for polarimetric characterization of a target with a system in accordance with the invention, as defined above, in particular in vivo characterization of a tissue, the method comprising:
  illuminating the target via the LLG,
  collecting with an optical detector light reflected by the target thus illuminated,
  selecting the probe state of at least one of a PSA and PSG and analyzing by controlling the PSA at least two different states of polarization of the light reflected by the target and directed to the optical detector and/or controlling the PSG to illuminate the target with at least two different states of polarization and analyzing the light reflected by the target, and
  computing from the corresponding light intensities measured with the detector at least one polarimetric parameter of the target.

The detection may be performed at one or more wavelengths, preferably at three wavelengths using a tri-CCD or tri-CMOS camera.

The detection may be performed through a detection channel made by a LLG distinct from the LLG serving to illuminate the target or by an imaging channel comprising an optical relay, such a succession of rod lenses in a rigid endoscope.

The method may comprise illuminating the target with polarized light via a PSG through which light is injected into the LLG and modulating the polarized state of the light that is injected.

The method may comprise:
  illuminating the target with a temporal succession of different polarization probe states, generated by the PSG, the polarized light propagating in the LLG,
  analyzing the thus illuminated target through the PSA and recording for each generator probe state and analyzer probe state corresponding intensity signals, in particular intensity images,
  determining the Mueller matrix $M_S$ of the target under observation based on the recorded intensity signals and knowledge of the polarimetric properties of the system obtained during beforehand calibration thereof.

During calibration of the system, the surface under observation may be an uniform reflecting unpolished surface, such as a metallic sandblasted plate, as it is (i.e. with no placement of additional optical components). The calibration may comprise the placement on the path of light of one or more polarizing optical elements. For example, for 4×4 Mueller polarimetry inter alia, the calibration may comprise the successive placement at one or more positions, for example three different positions, of at least three different polarizing optical elements, such as P0°, P90° and L30°, as detailed further below. These positions may include upstream the LLG, at the output of the LLG or at the input of the detection channel, and downstream of the detection channel.

DETAILED DESCRIPTION

Figure 1:
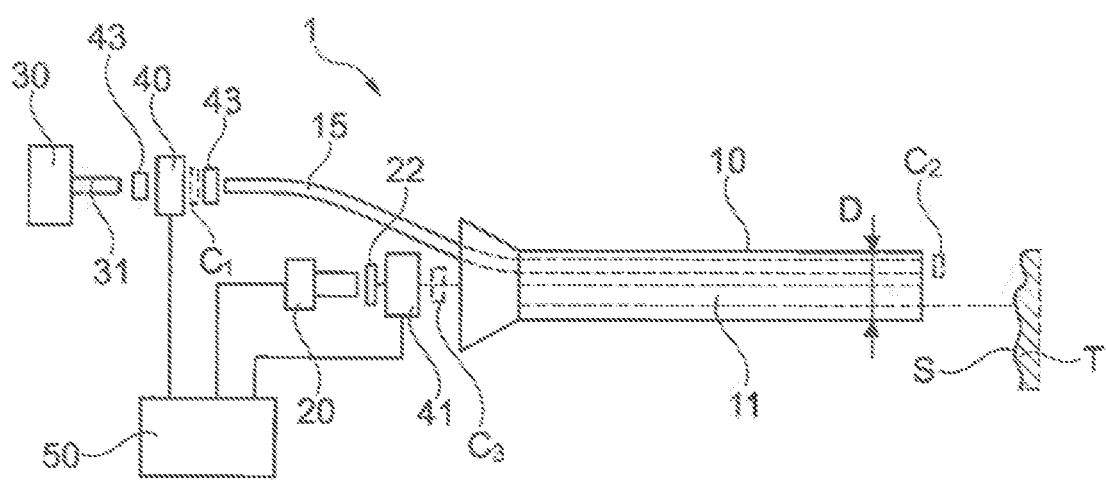
FIG. 1 is a partial and schematic view of an example of a Mueller polarimetry endoscopic system made in accordance with the invention.

The system 1 shown in FIG. 1 comprises a rigid casing 10 that is configured for introduction into a human or animal body to image a target S of a tissue T.

The casing 10 may comprise a tubular body that may be 15-35 cm long and is configured for introduction into the human or animal body.

The system 1 comprises a detection channel that extends inside the casing 10. The detection channel may be formed by a conventional endoscope 11.

Figure 3:
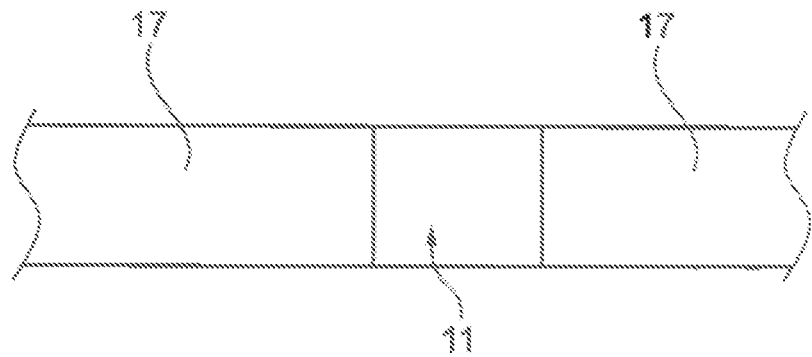
FIG. 3 is a partial and schematic axial section of the detection channel.

The detection channel may be made in a conventional manner with an optical relay which is preferably made of a succession of rod lenses 17, as shown in FIG. 3. The design of the detection channel may be based on the Hopkins rod lens design, which consists of a succession of lenses characterized by a length longer than their diameter and separation distance.

The detection channel may comprise an eyepiece near its proximal end and an Objective near its distal end. The objective forms an image of the target which is transmitted by the optical relay system up to the proximal end. The focal plane of the eyepiece may coincide with the image plane of the optical relay, so that the rays come out parallel from the eyepiece and create the image of the target at infinity.

The structure of the endoscope 11 is for example identical or similar to that of the laparoscope commercialized by the company Karl Storz under reference 26003 AA.

Figure 2:
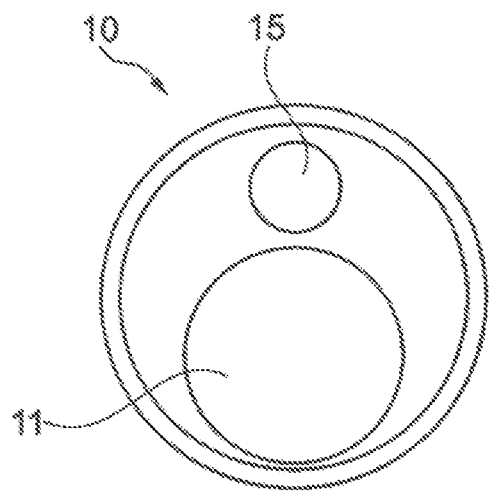
FIG. 2 is a schematic cross section of the system.

The endoscope 11 may be of circular or near circular cross section as shown in FIG. 2, of a diameter ranging for example from 2.5 to 10 mm.

In a variant, the detection channel is directly integrated into the rigid casing 10, without being part of a complete endoscope before introduction into the casing 10.

The system 1 also comprises an illumination channel that extends parallel to the detection channel inside the tubular body.

In accordance with the invention, the illumination channel is made of a liquid light guide (LLG) 15. The LLG can be identical or similar to that of a commercial liquid light guide commercialized for example by the company Thorlabs under reference LLG-04H, but the invention is not restricted to any particular kind of LLG.

The LLG 15 may be of circular or near circular cross section and of a diameter ranging from 2 to 8 mm for example.

The outside diameter D of the tubular body of the casing 10 is for example ranging from 10 to 20 mm, being preferably no greater than 12 mm.

The LLG 15 is closed at its ends in any appropriate known manner.

The system 1 comprises as optical detector a digital camera 20 that receives the light reflected by the surface S illuminated by the LLG 15.

The system 1 comprises a light source 30 to provide the light that is injected into the LLG 15.

A PSG 40 is interposed on the path of light between the light source 30 and the LLG 15 and a PSA 41 is interposed on the path of light between the endoscope 11 and the camera 20.

The PSG 40 and PSA 41 are controlled directly or indirectly by a computer or any other appropriate controller 50. This controller 50 may also be connected to the camera 20 for recording and processing the images thereof. The controller 50 enables the synchronization between the switch of the PSG and the PSA and the acquisition of the intensity images by the camera.

The light source 30 may be a white light source such as a Xenon lamp, LED lamp or halogen lamp, and light may be supplied from this source to the PSG by a fiber bundle 31 or any other appropriate optical system.

A monochromatic bandpass filter 22 may be interposed on the path of light between the PSA 41 and the camera 20, in which case the camera is monochromatic. One may also use a tri-CDD or tri-CMOS camera, and a tri-band filter.

The measurements may be made at a given wavelength between 340 and 1000 nm, for example between 450 nm to 700 nm, by selecting the bandpass filter 22.

In an example using a monochromatic camera 20, the bandpass filter 22 is a filter with a central wavelength of 550 nm and a bandwidth less than 30 nm FWHM. In another example, the filter 22 has a central wavelength of 532 nm with a spectral bandwidth of 10 nm FWMH. In another example, one uses a tri-band filter with a tri-CCD or tri-CMOS camera.

Light at the output of the PSG 40 is injected into the LLG 15.

Various optics 43, such as a system of lenses, may be placed before and/or after the PSG, for optimizing the injection of the light into the LLG, thus increasing the efficiency of light transmission.

The PSG 40 and PSA 41 are known per se and are electrically controlled. The PSG enables to produce four different states of polarization, and the PSA enables to produce four different configurations of analysis, as required by 4×4 Mueller polarimetry.

The PSG 40 comprises for example in a conventional manner a linear polarizer, a first electrically controllable liquid crystal cell, preferably a ferroelectric liquid crystal, a quarter wave plate and a second electrically controllable liquid crystal cell, preferably a ferroelectric liquid crystal, but other configurations of PSG may be used. The four Stokes vectors corresponding to the four polarization states thus generated are independent and can be arranged in four columns to form a 4×4 modulation matrix denoted W.

The PSA may comprise optical elements identical to that of the PSG but arranged in the reverse order relative to the direction of light propagation. The Stokes vectors corresponding to the four polarization configurations by the PSA are arranged in four rows to form a 4×4 analysis matrix denoted A.

For Mueller polarimetry, the PSG temporally modulate the polarization of light illuminating the target under observation by consecutively generating four independent probing polarization states. Each of the four polarization states produced by the PSG after interacting with the sample under observation is analyzed through four consecutive polarization configurations of the PSA. In this way, at least 16 measurements are sequentially performed over a finite interval of time and stacked in a real-valued matrix. This operation can be repeated multiple times in order to acquire the 16-components intensity matrix N times. This enables to improve the signal to noise ratio through an average process.

For each of the four polarization states produced by the PSG and analyzed through a polarization configuration of the PSA, the intensity measurement is performed for each pixel of the camera in imaging configuration.

The system is calibrated to account for the polarimetric properties of the optical components of the system and more particularly those of the LLG and of the detection channel.

Calibration may be performed in conventional manner by placing appropriate optical components after the PSG and before the PSA.

If one is willing to detail the polarimetric properties of the LLG and of the detection channel, they may be determined by measuring their Mueller matrices in a Triple Step Eigenvalue Calibration Method (T-S ECM) calibration process. Otherwise the system can be directly calibrated in a Single Step Eigenvalue Calibration Method (S-S ECM) calibration process. Both processes are detailed hereunder.

In such processes, a reflective surface S made of a sandblasted metallic plate is placed in front of the distal end of the imaging channel, and oriented perpendicularly to the longitudinal axis of the imaging channel.

If one wants to have detailed information about polarimetric properties of the optical components, in particular of the LLG 15 or of the imaging channel of the endoscope 11, one may use the Triple-Step Eigenvalue Calibration Method (T-S ECM).

In this case, the first step consists in performing a measurement without inserting any optical component in the system 1.

In this case the 16-components intensity matrix $B_0$ is obtained as:

$$B_0 \sim AM_{endo}M_{LLG}W \quad (1)$$

where $M_{endo}$ is the 4×4 Mueller matrix of the imaging channel of the endoscope 11 and $M_{LLG}$ is the Mueller matrix of the LLG 15.

Several optical components, in particular a polarizer with the transmission axis oriented at 0° with respect to a reference frame of the system (P0°), a polarizer with the transmission axis oriented at 90° (P90°) with respect to the transmission axis of P0° and a waveplate with one of its neutral axis oriented at 30° with respect to the transmission axis of P0°, are consecutively placed in C1.

In this case one obtains the 16-components intensity matrix $B_{1i}$ (i=P0°, P90°, L30°) given by:

$$B_{1i} \sim AM_{endo}M_{LLG}M_i W. \quad (2)$$

Then the optical components are consecutively placed in C2 to obtain the 16-components intensity matrix $B_{2i}$ (i=P0°, P90°, L30°) given by:

$$B_{2i} \sim AM_{endo}M_i M_{LLG} W \quad (3)$$

Then, they are consecutively placed in C3 to obtain the 16-components intensity matrix $B_{3i}$ (i=P0°, P90°, L30°) given by:

$$B_{3i} \sim AM_i M_{endo} M_{LLG} W. \quad (4)$$

By multiplying the inverse of (1) on the left for (2) and (3), as well as on the right for (3) and (4), the following equations can be obtained:

$$C_{1i} = B_0^{-1} B_{1i} = W^{-1} M_i W \quad (5)$$

$$C_{2Wi} = B_0^{-1} B_{2i} = W^{-1} M_{LLG}^{-1} M_i M_{LLG} W \quad (6)$$

$$C_{2Ai} = B_{2i} B_0^{-1} = AM_{endo} M_i M_{endo}^{-1} A^{-1} \quad (7)$$

$$C_{3i} = B_{3i} B_0^{-1} = AM_i A^{-1} \quad (8).$$

The matrices W and A can be obtained from (5) and (8) respectively following the procedure described in the article E. Compain et al "General and self-consistent method for the calibration of polarization modulators, polarimeters, and Mueller-matrix ellipsometers". Appl. Opt. 38, 3490-3502 (1999) or A. De Martino et al. "General Methods for optimized design and calibration of Mueller polarimeters", Thin Solid Films 455-456, 112-119 (2004).

Defining $\hat{W} = M_{LLG} W$ and $\hat{A} = AM_{endo}$ the equations (6) and (7) can be rewritten respectively as:

$$C_{2Wi} = W^{-1} M_{LLG}^{-1} M_i M_{LLG} W = \hat{W}^{-1} M_i \hat{W} \quad (9)$$

and:

$$C_{2Ai} = AM_{endo} M_i M_{endo}^{-1} A^{-1} = \hat{A} M_i \hat{A}^{-1} \quad (10)$$

The matrices $\hat{W}$ and $\hat{A}$ can be respectively obtained from (9) and (10) always following the procedure disclosed in E. Compain et al "General and self-consistent method for the calibration of polarization modulators, polarimeters, and Mueller-matrix ellipsometers". Appl. Opt. 38, 3490-3502 (1999) or A De Martino et al. "General Methods for optimized design and calibration of Mueller polarimeters", Thin Solid Films 455-456, 112-119 (2004).

The matrix $M_{endo}$ can be obtained from (1) using the formula:

$$M_{endo} = \hat{A}^{-1} B_0 \hat{W}^{-1} \quad (11)$$

Finally, $M_{LLG}$ can be obtained from (1) using the formula:

$$M_{LLG} = \tilde{A}^{-1} B_0 W^{-1}. \quad (12)$$

In this way, the polarimetric properties of the optical components of the system are characterized.

In order to measure the Mueller matrix $M_S$ of a target, the target is positioned in front of the system instead of the metallic plate.

Then, the 16-components intensity matrix $B_S$ is measured, given by:

$$B_S \sim \tilde{A} M_S \tilde{W}. \quad (13)$$

From (13) it is possible to use the matrices $\tilde{W}$ and $\tilde{A}$, previously determined using the T-S ECM, in order to obtain the Mueller matrix $M_S$ of the target by means of:

$$M_S \sim \tilde{A}^{-1} B_S \tilde{W}^{-1}. \quad (14)$$

If a detailed polarimetric characterization of the LLG or of the detection channel is not needed, the Single Step Eigenvalue Calibration Method (S-S EMS) can be used.

In this case, the first step consists in performing a measurement without inserting any optical component in the system 1.

In this case the 16-components intensity matrix $B_0$ in (1) is obtained. Then, the calibration optical elements are consecutively placed in C2 in order to obtain the 16-components intensity matrix $B_{2i}$ in (3).

By multiplying on the left the inverse of (1) for (3) it is possible to obtain (6).

Defining $\hat{W} = M_{LLG} W$ the equation (9) can be obtained from which $\hat{W}$ can be derived by using the procedure described in E. Compain et al "General and self-consistent method for the calibration of polarization modulators, polarimeters, and Mueller-matrix ellipsometers", Appl. Opt. 38, 3490-3502 (1999) or A De Martino et al. "General Methods for optimized design and calibration of Mueller polarimeters", Thin Solid Films 455-456, 112-119 (2004).

Then the matrix $\tilde{A} = AM_{endo}$ can be Obtained from (1) as:

$$A\tilde{A} = B_0 \tilde{W}^{-1}. \quad (15)$$

Then the 4×4 Mueller matrix $M_S$ of a sample can be derived from (14) by using $\hat{W}$ and $\hat{A}$ determined during calibration.

Polarimetric parameters, such as tor example the depolarization, retardance and dichroism, can be extracted from the measured Mueller matrix $M_S$ by using for example the Lu-Chipman decomposition, which is widely used in polarimetry and which describes a Mueller matrix as a product of three matrices corresponding respectively to a depolarizer, a retarder and a diattenuator, from which polarimetric properties can be extracted (see S.-Y. Lu and R. A. Chipman "Interpretation of Mueller matrices based on polar decomposition", J. Opt. Am. A13, 1106(1996))

The invention is not limited to the above described embodiments.

In a variant where one desires to measure the 3×Mueller matrix, it is enough for the PSG to produce 3 different probe polarization states and for the PSA to produce 3 different polarization probe configurations.

Each probe polarization produced by the PSG is analyzed through the three probe polarization configurations of the PSA for a total of 9 intensity measurements.

In this case the system 1 may be calibrated with the Eigenvalue Calibration Method slightly modified as explained in the article Eigenvalue calibration method for 3×3 Mueller polarimeters from Ji Qi et al, 2362 Vol 44, No. 9/1 May 2019 Optics Letters.

For Stokes polarimetry, the PSA is left while the PSG is replaced by a polarizer (linear, circular or elliptical). In a variant, the PSG is left, and the PSA is replaced by a polarizer (linear, circular or elliptical).

For Orthogonal State Contrast (OSC) polarimetry, the intensity measurement is performed by controlling the PSA in order to produce a polarization configuration that is either parallel ($I_{parallel}$) or perpendicular ($I_{perpendicular}$) to the polarization state produced by the PSG, or by controlling the PSG in order to produce polarization states that are either parallel ($I_{parallel}$) or perpendicular ($I_{perpendicular}$) to the polarization configuration of the PSA.

The intensity of the OSC is obtained by:

$$I_{OSC} = \frac{I_{parallel} I_{perpendicular}}{I_{parallel} + I_{perpendicular}} \quad (14)$$

This type of measurement enables to characterize only pure depolarizers. OSC can also be performed using circular polarization or elliptical polarization.

Figure 4:
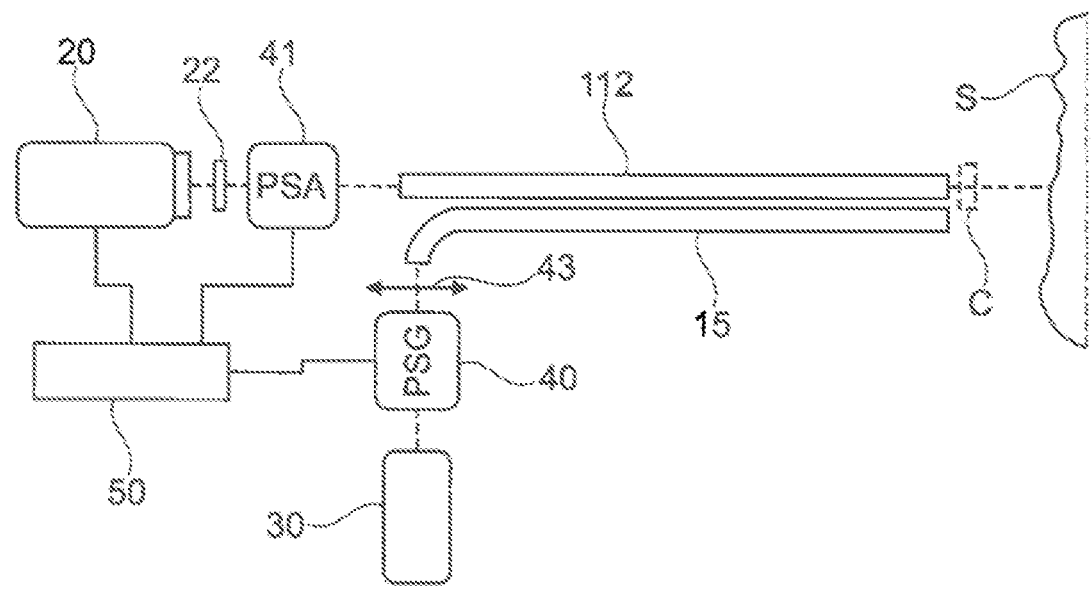
FIG. 4 is a schematic view of a first variant embodiment of the invention.

The system 1 may comprise a second LLG 112 to collect the reflected light, instead of the endoscope 11, as illustrated in FIG. 4. The second LLG used to collect the reflected light from the sample is different from the LLG used to illuminate the sample.

In that example, the camera is replaced with a photodiode detector 20 for rapid single point detection. In that variant, there is no imaging of the target. Such a system is mainly useful to characterize large areas of targets with spatially uniform polarimetric properties.

The system of FIG. 4 may be used for 4×4 or 3×3 Mueller polarimetry.

Calibration optical components can be placed at C, in front of the LLG 112, for calibration with S S-ECM.

Figure 5:
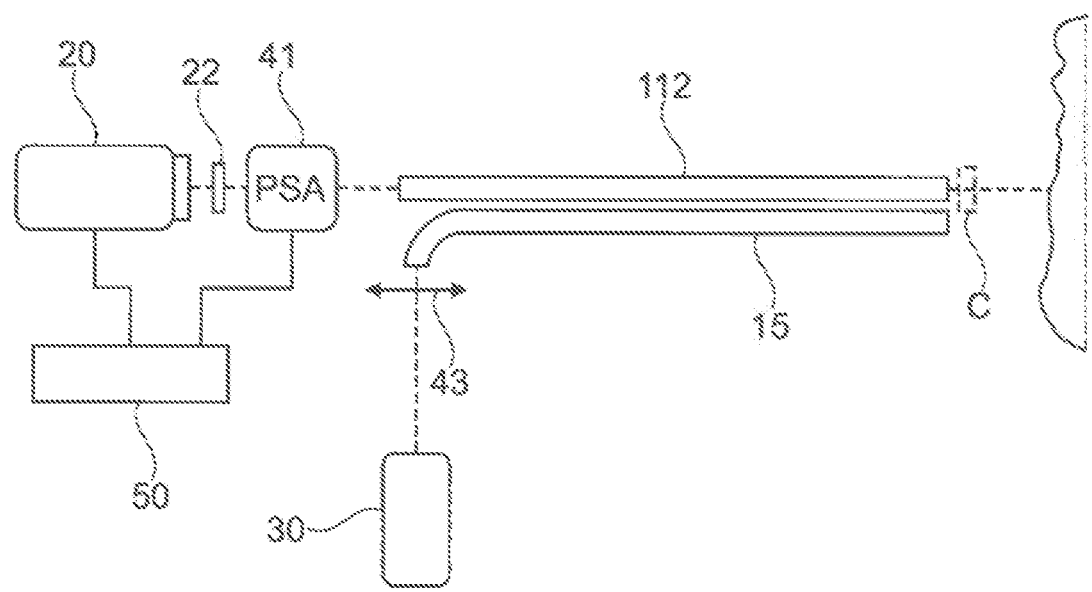
FIG. 5 is a schematic view of a second variant embodiment of the invention.

In the example of FIG. 5, the difference with FIG. 4 is that there is no PSG but only the PSA 41. Totally depolarized light can be injected in the LEG for Stokes polarimetry.

Otherwise, for OSC or Stokes polarimetry, a polarizer (not shown), such as a linear, circular or elliptical polarizer, can replace the PSG for injecting polarized light into the LLG.

For Stokes polarimetry, the PSA will take successively four probe states. For OSC polarimetry, the PSA will take successively two probe states.

In a variant (not shown), the configuration is the one of FIG. 5 except that the PSA is removed or replaced by a polarizer. The PSG is reintroduced.

Figure 6:
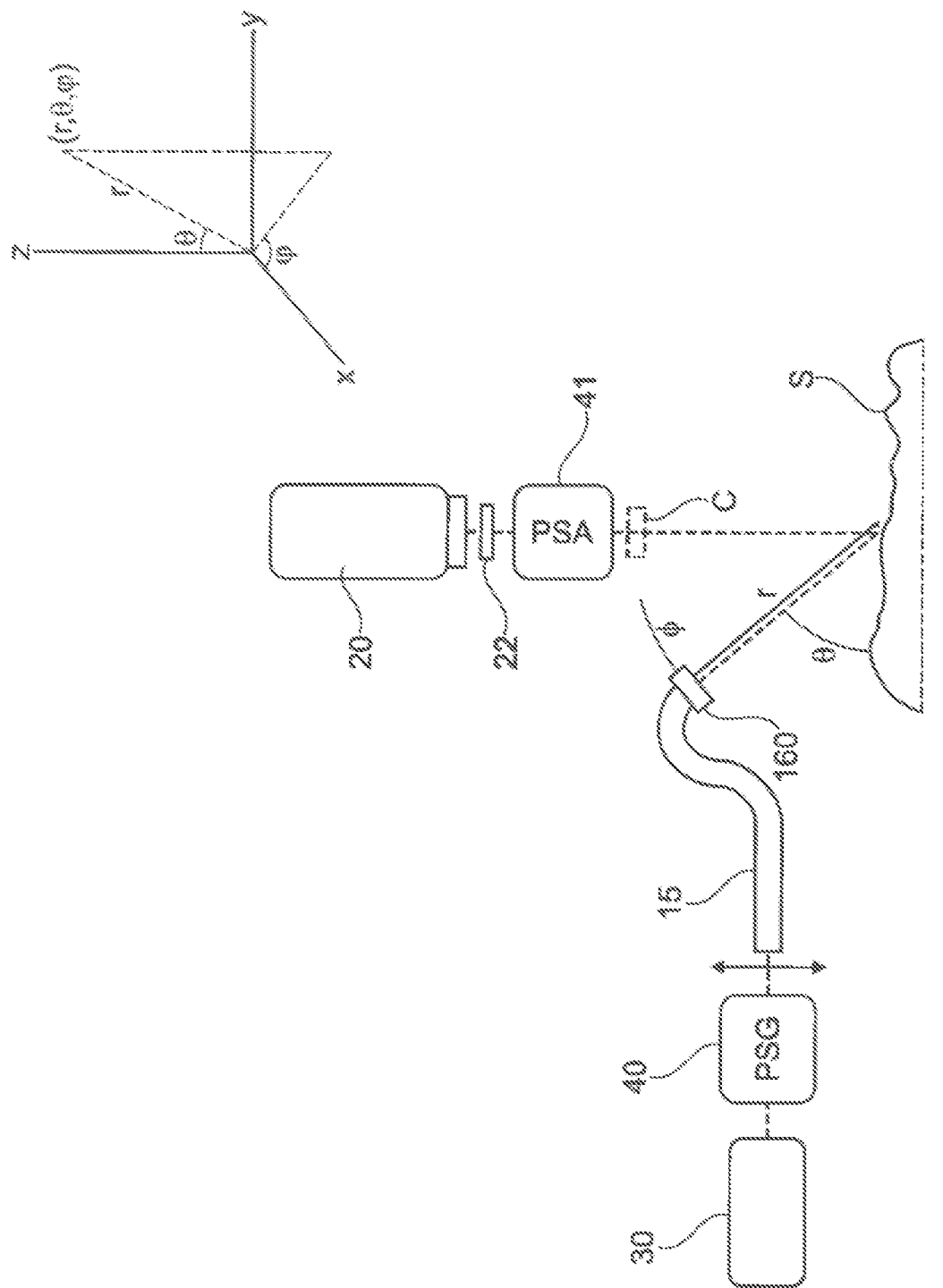
FIG. 6 is a schematic view of a third variant embodiment of the invention.

In the embodiment of FIG. 6, reflected light propagates from the target to the PSA 41 without being guided by a LLG or an endoscopic imaging channel with rod lenses as described above or another optical system. The target is illuminated by the LLG 15, which can be fixed on a mount 160 holding its distal tip. The mount may be mobile, being carried for example by a motorized arm, enabling to vary its azimuth angle around the optical axis z of the PSA 41, and/or to vary the distance from the target and/or to vary the incidence angle. Adapted optics (not shown) can be placed at the output of the LLG to obtain different sizes for the beam to illuminate the sample. Such an embodiment can be used for in vivo and ex vivo polarimetry, or for non-medical applications where there is room for moving the LLG around the imaging axis. Acquiring the polarimetric response as a function of the incident angle may serve to generate data for reconstructing a 3D structure of the target, for example. The embodiment of FIG. 6 may be used for 4×4 Mueller polarimetry, 3×3 Mueller polarimetry, Stokes polarimetry or OSC polarimetry.

In all above described embodiments, the PSG and PSA can be based on components other than ferroelectric liquid crystals, for example photo-elastic modulators (PEMs) or nematic liquid crystals. The PSG and PSA can also be simplified whenever possible to produce less than 4 polarized states, for example if 3×3 Mueller matrix, Stokes polarimetry or OSC is desired. The PSG and PSA should preferably be sufficiently fast to acquire images in 2 seconds maximum and allow a large field of view ideally for in vivo applications.

The optical detector may also be a Division of Focal Plan polarization camera consisting of a micro-polarizer array as for example commercialized by the company 4D Technology inc. under reference PolarCam. In this case the PSA can be simplified, it no longer requires any polarizer and only 2 retarder configurations are necessary instead of the usual 4 to measure a 4×4 Mueller Matrix.

The invention may be used for polarimetric characterization of targets other than human or animal tissues. Any application where endoscopes are necessary could be interesting for the invention. This can include industry applications where bulky optical components cannot be used or where remote inspection is required.

The invention claimed is:

1. A system for polarimetric characterization of a target, comprising:
   a liquid light guide (LLG) for propagating light from a light source to the target,
   at least one of:
     a Polarization State Analyzer (PSA) serving to analyze the polarization of the light having propagated into the LLG and that has been reflected/backscattered by the target, and
     a Polarized State Generator (PSG) for modulating the polarization of light injected into the LLG,
   a camera for detecting light reflected/backscattered by the target that has been illuminated by the LLG, and
   a detection channel separate from the LLG used for the illumination, and in which light propagates before reaching the camera.

2. The system of claim 1, wherein the LLG extends along the detection channel.

3. The system of claim 1, wherein the detection channel extends in a rigid endoscope.

4. The system of claim 1, wherein the LLG and the detection channel extend in a rigid casing.

5. The system of claim 1, further comprising both a PSG through which light is injected into the LLG and a PSA through which light reaches the camera.

6. The system of claim 1, wherein the light from the target is detected by the camera without having the light reflected/backscattered by the target propagating through a LLG.

7. The system of claim 1, further comprising a control system to control the PSA and/or PSG, record signals from the camera and compute polarimetric parameters and/or the Mueller matrix of the target and display corresponding information.

8. The system of claim 1, further comprising a bandpass filter or a tri-band filter for narrowing the bandwidth of the light that is reaching the camera, the bandwidth is no greater than 30 nm.

9. A method for polarimetric characterization of a target with a system as defined in claim 1, the method comprising:
   Illuminating the target via the LLG, collecting with the camera light reflected/backscattered by the target thus illuminated, wherein the collection of light is performed through a detection channel distinct from the LLG, selecting a probe state of at least one of a PSA and PSG and controlling the PSA to analyze at least two different states of polarization of the light reflected/backscattered by the target and directed to the camera and/or controlling the PSG to illuminate the target with at least two different states of polarization and analyzing the light reflected/backscattered by the target, and computing from the corresponding light intensities measured with the camera at least one polarimetric parameter of the target.

10. The method of claim 9, wherein the collection of light is performed at one or more wavelengths.

11. The method of claim 9, the detection channel being an imaging channel comprising a succession of rod lenses in a rigid endoscope.

12. The method of claim 9, further comprising illuminating the target with polarized light, via a PSG through which light is injected into the LLG, and modulating the polarized state of the light that is injected.

13. The method of claim 12, comprising:

Illuminating the target with a temporal succession of different polarization probe states, generated by the PSG, the polarized light propagating in the LLG, analyzing the thus illuminated target through the PSA and recording for each generator probe state and analyzer probe state corresponding intensity signals, determining the Mueller matrix $M_s$ of the target under observation based on the recorded intensity signals and knowledge of the polarimetric properties of the system obtained during beforehand calibration thereof.

14. The system of claim 1, wherein the detection channel is an imaging channel comprising a succession of rod lenses.

15. The system of claim 2, wherein the LLG extends at least on part of its length parallel to the detection channel.

16. The system of claim 4, wherein the casing comprises a tubular body.

17. The system of claim 5, wherein the PSG and/or PSA comprises ferroelectric liquid crystals.

18. The system of claim 8, wherein the bandwidth is no greater than 20 nm.

19. The method of claim 10, wherein the collection of light is performed at three wavelengths using a tri-CCD or tri-CMOS camera.

20. The system of claim 1, wherein the LLG has a diameter ranging from 2 mm to 8 mm.

21. The system of claim 1, wherein the camera is a polarization camera.

* * * * *